United States Patent [19]
Karimian et al.

[11] Patent Number: 5,817,875
[45] Date of Patent: Oct. 6, 1998

[54] METHODS FOR THE MANUFACTURE OF TERBINAFINE

[76] Inventors: Khashayar Karimian, 18 Pine Cliff Drive; Regis C. H. S. Leung-Toung, 3620 Kaneff Crescent, #1412, both of Mississauga, Ontario, Canada, L5N 3X1; Yiwei Li, 101 Subway Crescent, #1201, Etobicoke, Ontario, Canada, M9B 6K4; Tim Fat Tam, 155 Veneto Drive, Woodbridge, Ontario, Canada, L4L 8X6

[21] Appl. No.: 716,124

[22] Filed: Sep. 19, 1996

[30] Foreign Application Priority Data

Sep. 20, 1995 [NZ] New Zealand .............................. 280065

[51] Int. Cl.[6] .................................................. C07C 209/68
[52] U.S. Cl. ........................ 564/387; 564/393; 564/413; 564/428
[58] Field of Search ..................... 564/393, 413, 564/428, 387

[56] References Cited

FOREIGN PATENT DOCUMENTS 1157023  11/1983  Canada ............................... 260/217.1

OTHER PUBLICATIONS

"Allylamine Antimylotics: Recent Trends in Structure—Activity Relationships and Syntheses"—Peter Nussbaumer, Neil S. Ryder & Anton Stüz, Aug. 1990, pp. 437–455 Pestic. Sci.

"A New Route to the Synthesis of Terbinafine"—Seok Jong Lee, Jae Ho Lee, Kyong Up Baik, and Myung Hwan Park, Jul. 31, 1997, pp. 1218–1220, Bull. Korean Chem. Soc. 1997, vol. 18, No. 11.

Primary Examiner—Brian M. Burn
Attorney, Agent, or Firm—Nixon & Vanderhye P.C.

[57] ABSTRACT

Process for the manufacture of naphthylmethylamine derivatives and among them terbinafine as potential antimycotic agents.

21 Claims, No Drawings

5,817,875

METHODS FOR THE MANUFACTURE OF TERBINAFINE

FIELD OF THE INVENTION

This invention relates to novel processes for the manufacture of trans-N-methyl-N-(1-naphthylmethyl)-6,6-dimethylhept-2-en-4-ynyl-1-amine, novel intermediates of formula II useful in the manufacture of such naphthylmethylamines, and novel processes for the manufacture of the intermediates used.

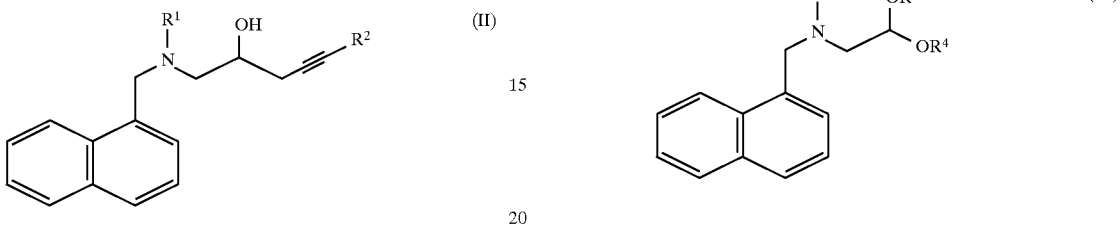

wherein:
$R^1$ is lower alkyl
$R^2$ is alkyl, branched alkyl, aryl.

Alkyl groups include straight and branched chain hydrocarbon radicals having 1 to 8 carbon atoms.

The lower/alkyl groups include straight and branched chain hydrocarbon radicals from 1 to 4 carbon atoms.

Aryl as used herein include phenyl or naphthyl.

According to further aspects of this invention, there are provided methods for the conversion of compounds of formula II to terbinafine and naphthylmethylamines derivatives of formula I.

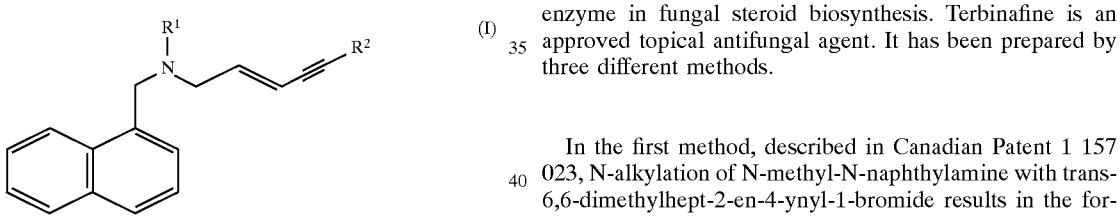

wherein:
$R^1$ is lower alkyl
$R^2$ is alkyl, branched alkyl, aryl.

A third aspect of this invention relates to a process of reacting an aldehyde of formula (V) with a Wittig reagent of formula (VI), or with a reagent of formula (VII) to give compound of formula (I),

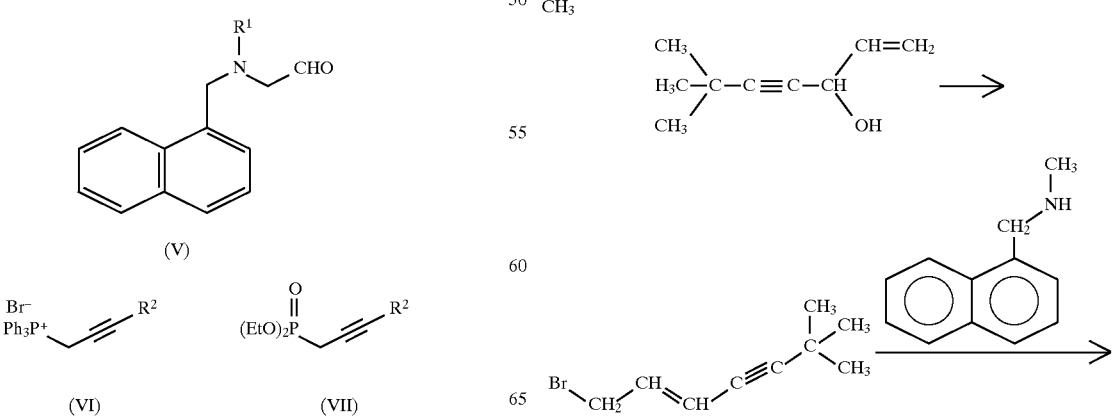

wherein:

$R^1$ and $R^2$ have the same definition as described above.

A fourth aspect of this invention concerns the use of compounds of formula (IV) as a precursor in the synthesis of compounds of formula (I), wherein $R^1$ has the same definition as above and $R^3$, $R^4$ are independently lower alkyl, or when $R^3$ and $R^4$ are taken together, form an ethylene linkage of —$CH_2CH_2$—.

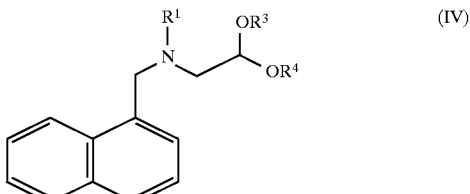

BACKGROUND OF INVENTION

This invention relates to certain N-alkyl-N-(1-naphthylmethyl)-2-hydroxyalkyl-4-ynyl-1-amines as potential antimycotic agents. Several articles have been published emphasising the pharmaceutical properties of terbinafine, see Petranyl, G. et. al., *Science*, 1984, 24, 1239; Stutz.A. et. al., *J. Med. Chem.*, 1984, 27, 1539. Terbinafine is a powerful inhibitor of fungal squalene epoxidase which serves as a key enzyme in fungal steroid biosynthesis. Terbinafine is an approved topical antifungal agent. It has been prepared by three different methods.

In the first method, described in Canadian Patent 1 157 023, N-alkylation of N-methyl-N-naphthylamine with trans-6,6-dimethylhept-2-en-4-ynyl-1-bromide results in the formation of terbinafine. The trans-6,6-dimethylhept-2-en-4-ynyl-1-bromide is prepared from 6,6-dimethylhepten-4-ynyl-3-ol and hydrogen bromide as illustrated in Scheme 1.

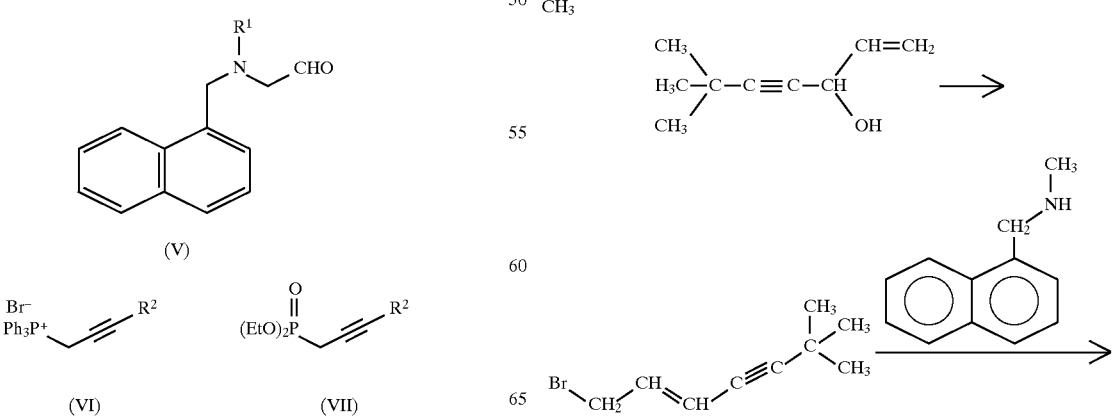

-continued
Scheme 1

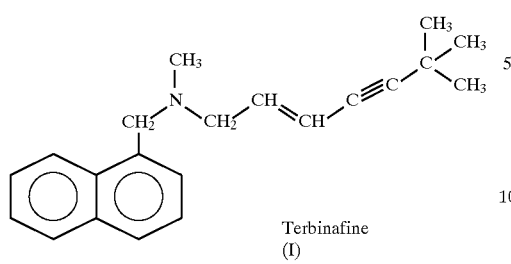

Terbinafine
(I)

In the second method also described in Canadian Patent 1 157 023, N-methyl-N-(1-naphthylmethyl)-6,6-dimethylhept-2-4-diynyl-1-amine is reduced by catalytic hydrogenation to give terbinafine. The key intermediate N-methyl-N-(1-naphthylmethyl)-6,6-dimethylhept-2-4-diynyl-1-amine is prepared from N-methyl-N-naphthylamine and 6,6-dimethylhept-2-4-diyne, or from the acetylene coupling reaction between N-methyl-N-naphthylmethylpropargyl amine and tert-butylacetylene bromide as depicted in Scheme 2.

Scheme 2

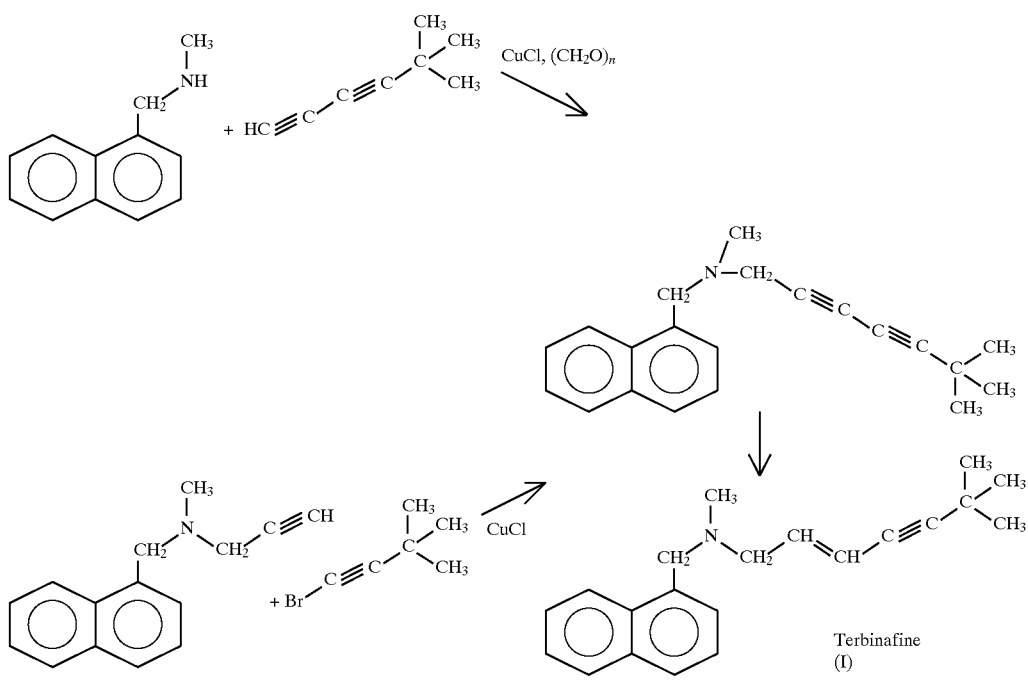

Terbinafine
(I)

Canadian Patent 1 157 023, further relates to a 3rd method of preparing terbinafine by reductive amination of the naphthylamine with trans-6,6-dimethylhept-2-en-4-yn-1-al in the presence of formaldehyde and sodium borohydride. The reaction is described in Scheme 3.

Scheme 3

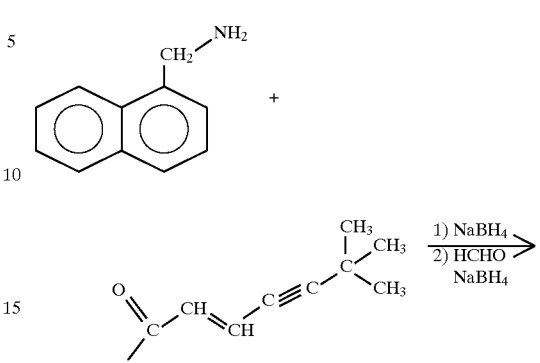

-continued
Scheme 3

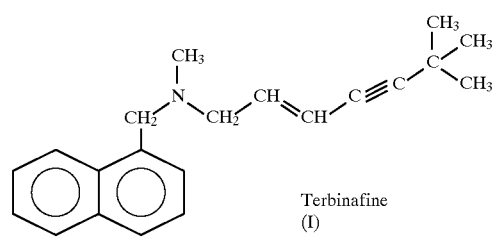

Terbinafine
(I)

When compared to the above processes, the applicant's invention introduces a number of advantages over the existing processes:

First, it affords terbinafine in considerably higher yields than existing procedures.

Second, it is amenable to industrial scale production since terbinafine can be made in three steps from commercially available starting material.

Third, it avoids the use of intermediates such as trans-6,6-dimethylhept-2-en-4-yn-1-al, 6,6-dimethylhept-2-4-diyne, and trans-6,6-dimethylhept-2-en-4-ynyl-1-bromide. All of those intermediates derives from multistep synthesis thereby rending the process more expensive.

Fourth, it avoids the use of acreloin (Scheme 1) which is a very hazardous chemical and not commercially available in pure form.

Fifth, it avoids the use of toxic and volatile reagents such as formaldehyde.

Therefore, one object of the present invention is to provide novel process for the production of terbinafine from readily available, inexpensive and relatively safe starting materials. Other objects of this invention can be recognized by those skill in the art from the summary of invention and detailed description of embodiments thereof.

SUMMARY OF INVENTION

According to one aspect of the present invention, a process is provided to make terbinafine which comprises of the steps of conversion of N-alkyl-N-naphthylmethylamine to their corresponding 2,3-epoxypropane (III) as shown in Scheme 4. Compound III is then reacted with lithium alkylacetylide in the presence of lewis acid to give N-alkyl-N-(1-naphthylmethyl)-2-hydroxyheptan-4-ynyl-1-amine, a compound of formula II. Dehydration of the alcohol II affords a mixture of E and Z-terbinafine.

Scheme 4

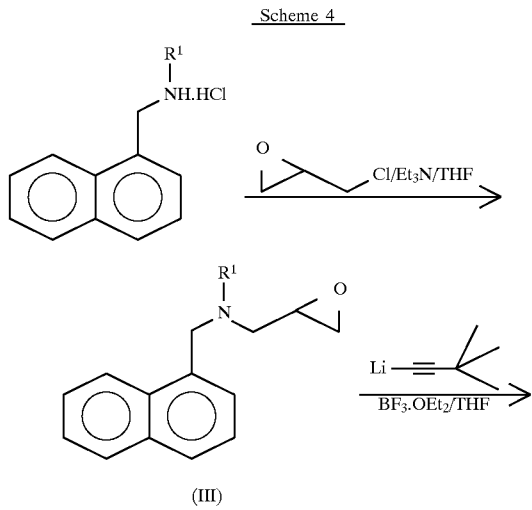

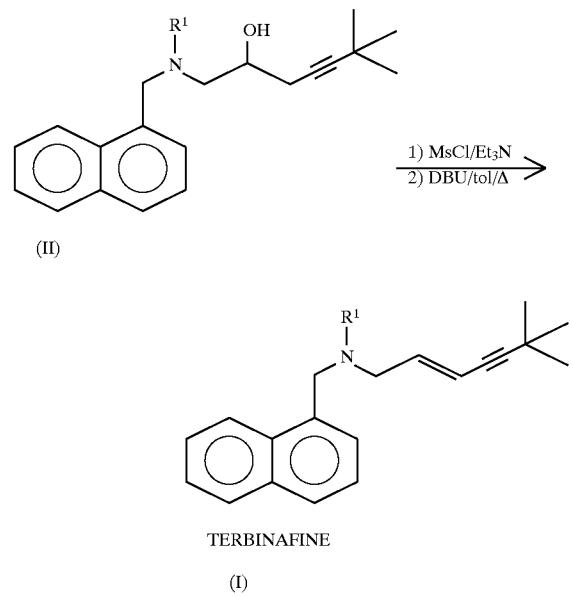

A second process includes the reaction between an aldehyde of formula (V) with a Wittig reagent (VI), or with a reagent (VII) to afford the enyne compound of formula I (Scheme 5). Reaction of N-alkyl-N-naphthylmethylamine with bromo acetaldehyde dialkyl acetal gives the compound of formula (IV), which can be hydrolysed in acid to give the aldehyde (V).

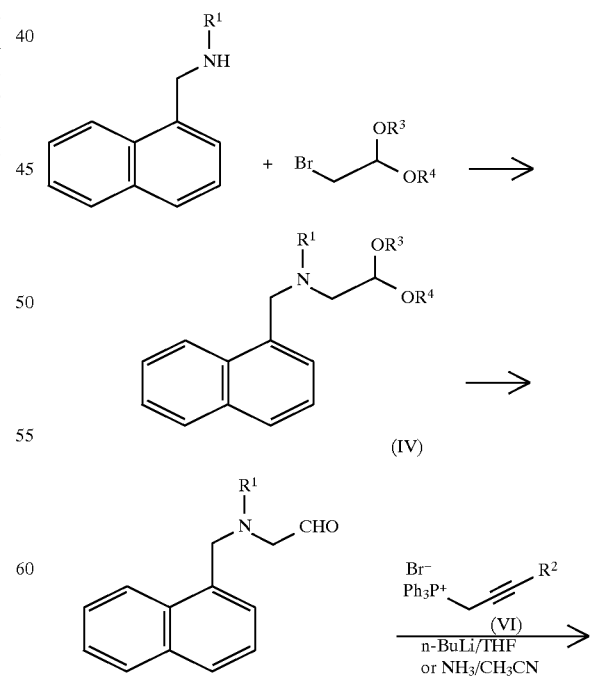

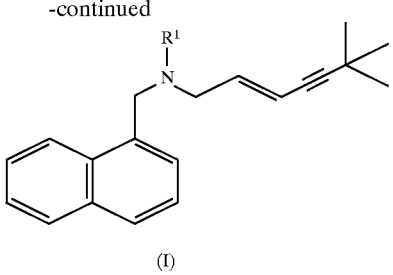

(I)

DETAILED DESCRIPTION OF INVENTION

In the first process of this invention, N-methyl-N-naphthylmethylamine is reacted with epichlorohydrin in the presence of a strong base such as sodium hydroxide, sodium methoxide or tetrabutylammonium hydroxide in alcohol to give the N-methyl-N-naphthylmethyl-2,3-epoxypropane (III). N-Methyl-N-naphthylmethylamine could, in principle, react with epichlorohydrin to give the diamine derivative 1,3-di-(N-methyl-N-naphthylmethylamino)propan-2-ol because the epoxide (III) may undergo further reaction with excess amine. To prevent the formation of this undesirable side product, N-methyl-N-naphthylmethyl is reacted with excess epichlorohydrin to give the N-methyl-N-naphthylmethyl-2,3-epoxypropane (III) as the major product. The excess epichlorohydrin can be removed by distillation. The preferred condition requires the use of 5 to 10 equivalents of epichlorohydrin, in the presence of sodium hydroxide, in methanol at 60° C. for a period of 3 hrs. The epoxide (III) is isolated by conventional means.

The epoxide (III) does not react with lithium tert-butylacetylene in an inert solvent such as tetrahydrofuran. However, the reaction proceeds smoothly in presence of boron trifluoride ethereate at −78° C. The most preferred condition for this transformation requires the mixing of lithum tert-butylacetylene and epoxide (III) at −20° C., followed by the addition of boron triflouride ethereate. The product can be isolated by conventional methods.

The hydroxyl function of the resulting alcohol (II) is converted to the corresponding methanesulfonate or tosylate, or other good leaving groups, in the presence of a base such as triethylamine, and methanesulfonyl chloride or toluenesulfonyl chloride at low temperature, preferably at 0° C. Treatment of the resulting material with a strong base such as 1,8-diazabicyclo[5.4.0]undec-7-ene (DBU) or 1,5-diazabicyclo[4.3.0]undec-7-ene (DBN), tert-butoxide, potassium hydroxide and the like affords the E/Z terbinafine as a mixture. The E isomer is separated by recrystallization as a hydrochloride salt. In another embodiment, the alcohol (II) can be directly dehydrated to give a mixture of E/Z terbinafine by heating in dimethyl sulfoxide (DMSO), preferably at reflux temperature. In a further embodiment, the alcohol (II) can be dehydrated under acidic conditions to afford a mixture of E/Z terbinafine. For example, heating the alcohol (II) in DMSO containing silica gel and p-toluenesulfonic acid or heating the alcohol (II) in toluene containing Amberlyst 15.

In the second process of this invention, N-methyl-N-naphthylmethylamine reacts with bromoacetaldehyde dialkylacetal in the presence of a base to give a compound of formula (IV) which undergoes acid hydrolysis to afford the aldehyde of formula (V). Examples of bases used in the N-alkylation are sodium hydroxide and potassium carbonate. Compound of formula (IV) will undergo acid hydrolysis with diluted mineral acid such as dilute hydrochloric acid at elevated temperature to give the aldehyde. Alternatively, the hemiacetal (IV) can be deprotected by stirring the compound in acetone in the presence of p-toluenesulfonic acid at room temperature. The aldehyde reacts with the Wittig reagent (VI) or the reagent (VII) in the presence of base such as ammonia in acetonitrile or n-butyllithium in tetrahydrofuran to give the E/Z terbinafine as a mixture.

The starting materials are prepared following processes well documented in the art. The Wittig reagent (VI) is prepared from 1-bromoalkyne and triphenylphosphine according to literature procedures, see Eiter, K.; Oediger, H., *Liebigs Ann. Chem.* 1965, 62, 682, Corey, E. J.; Ruden, R. A., *Tetrahedron Lett.* 1973, 1495 and 1-bromoalkyne can be prepared by the procedures outlined in Brandsma, L. et. al, in *Synthesis of Acetylenes, Allenes and Cumulenes, a laboratory manual,* p. 221, Elsevier Scientific Publishing Company, 1981. Preparation of compound (IV) is carried out according to the procedure reported in Sandler, S. R. and Karo, W., in *Organic Functional Group Preparation,* p. 385, Academic Press, Inc., 1983 and the hydrolysis of compound (IV) to aldehyde (V) is accomplished following standard procedures taken from Greene, T. W., in *Protective Groups in Organic Synthesis,* pp119–127, John Wiley & Sons, 1981.

The present invention will be more fully understood by the following examples which illustrate the invention, but are not considered limiting to the scope of the invention.

EXAMPLE I
N-Methyl-N-naphthylmethyl-2,3-epoxypropane (III)

(i) To an ice-cooled solution of N-methyl-1-naphthalenemethylamine hydrochloride (2.1 g) in methanol (40 mL) and water (10 mL) was added sodium hydroxide powder (2 g) followed by dropwise addition of epichlorohydrin (8 mL). The mixture was heated at 60° C. for 3 h then cooled to room temperature. Volatile materials were removed in vacuo and the residue was taken up in ethyl acetate and washed with water. The organic phase was collected, dried over sodium sulfate, filtered and evaporated to dryness. The crude mixture was purified by flash chromatography on silica gel (grade 9385, Merck, 230–400 mesh, 60 A) using a solvent gradient of a mixture of hexane and ethyl acetate (95:5, 90:10 and 85:15) as eluent, thereby affording the title compound (III) (1.85 g, 81.5%) as an oil.

$^1$H-NMR (CDCl$_3$) δ (ppm): 8.37 (m, 1H); 7.80–7.91 (m, 2H); 7.44–7.58 (m, 4H); 4.11 (d, J=13.0 Hz, 1H); 3.92 (d, J=13 Hz, 1H); 3.17 (m, 1H); 2.85 (dd, J=13.4 and 3.6 Hz, 1H); 2.78 (m, 1H); 2.49 (dd, J=5.0 and 2.7 Hz, 1H); 2.44 (dd, J=13.4 and 6.5 Hz) and 2.40 (s, 3H).

$^{13}$C-NMR (CDCl$_3$) δ (ppm): 134.6, 133.9, 132.5, 128.5, 128.1, 127.5, 125.9, 125.7, 125.1, 124.7, 61.0, 60.0, 50.9, 45.1, 43.2.

HRMS: calc. for $C_{15}H_{17}NO$ 227.1310 found 227.1315.

(ii) Similarly, the title compound (III) can be obtained when sodium methoxide is employed as base.

(iii) Similarly, the title compound (III) can be obtained when the phase transfer reagent, tetrabutylammonium hydroxide is employed as base.

EXAMPLE II
N-Methyl-N-(1-naphthylmethyl)-2-hydroxy-heptan-4-ynyl-1-amine (II)

To a solution of 3,3-dimethylbutyne (2.95 mL) in dry THF (50 mL) at −78° C. was added a 2.5M solution of n-BuLi in hexane (10 mL) dropwise. The mixture was allowed to warm to room temperature over 15 min and stirred at that temparature for a further 15 min, then was cooled back to −78° C. and BF$_3$.OEt$_2$ (3 mL) was added dropwise. The mixture was stirred for 15 min and 1.8 g of N-Methyl-N-naphthylmethyl-2,3-epoxypropane (III), dissolved in THF (10 mL), was added dropwise. After stirring at −78° C. for 2 h, saturated sodium bicarbonate solution (15 mL) was added, and the reaction mixture was allowed to warm to room temperature. The mixture was extracted with ethyl acetate (2×25 mL), and the combined organic fractions was dried over sodium sulfate, filtered and concentrated in vacuo. The residue was purified by flash chromatrography on silica gel (grade 9385, Merck, 230–400 mesh, 60 Å) using a mixture of hexane and ethyl acetate (85:15) as eluent, thereby affording the title compound as an oil (1.95 g, 79%).

$^1$H-NMR (CDCl$_3$) δ (ppm): 8.23 (m, 1H); 7.78–7.87 (m, 2H); 7.40–7.57 (m, 4H); 4.08 (d, J=13.0 Hz, 1H); 3.92 (d, J=13 Hz, 1H); 3.82 (m, 1H); 3.62 (m, 1H); 3.48 (m, 1H); 2.60 (d, J=6.5 Hz, 2H); 2.31 (s, 3H) and 1.22 (s, 9H).

$^{13}$C-NMR (CDCl$_3$) δ (ppm): 134.2, 134.0, 132.4, 128.6, 128.3, 127.7, 126.1, 125.7, 125.1, 124.3, 91.2, 74.2, 66.4, 62.4, 61.4, 42.3, 31.3, 27.4, 22.7.

HRMS: calc. for $C_{21}H_{27}NO$ 309.2093 found 309.2108

EXAMPLE III
NmethylN(1naphthylmethyl)6.6dimethylhept2en4ynyl)1amine (I)

(i) To an ice-cooled solution of N-methyl-N-(1-naphthylmethyl)-2-hydroxy-heptan-4-ynyl-1-amine (II) (155 mg) in THF (10 mL) was added Et$_3$N (0.35 mL) followed by methanesulfonyl chloride (0.075 mL). The resulting mixture was stirred at 0° C. for 3 h, then filtered. The filtrate was concentrated in vacuo, dissolved in toluene (10 mL) and DBU (0.37 mL) was added. The resulting mixture was heated at 80° C. for 4 h, cooled to room temperature then poured onto a silica gel column and eluted with hexane (100%) followed by a mixture of hexane and ethyl acetate (95:5). Thus, a mixture of E- and Z-isomers of N-methyl-N-(1-naphthylmethyl)-6,6-dimethylhept-2-en-4-ynyl)-1-amine were obtained in a ratio of 2:5 (95 mg, 66%).
E-isomer (Ia); N-Methyl-N-(1-naphthylmethyl)-6,6-dimethyl-hept-2(trans)-en-4-ynyl)-1-amine $^1$H-NMR (CDCl$_3$) δ (ppm): 8.30 (m, 1H); 7.80–7.86 (m, 2H); 7.27–7.61 (m, 4H); 6.20–6.29 (dt, J=16.0 and 6.5 Hz, 1H), 5.75 (dt, J=16.0 and 1.5 Hz, 1H), 3.95 (s, 2H); 3.20 (dd, J=6.5 and 1.5 Hz, 2H); 2.21 (s, 3H) and 1.33 (s, 9H).

$^{13}$C-NMR (CDCl$_3$) δ (ppm): 134.9, 134.8, 133.9, 132.5, 128.5, 128.0, 127.3, 125.9, 125.6, 125.2, 124.7, 112.9, 98.4, 77.3, 60.1, 59.7, 42.4, 31.1 and 28.0.

Z-isomer (Ib); N-Methyl-N-(1-naphthylmethyl)-6,6-dimethyl-hept-2(cis)-en-4-ynyl)-1-amine $^1$H-NMR (CDCl$_3$) δ (ppm): 8.25 (m, 1H); 7.71–7.86 (m, 2H); 7.38–7.55 (m, 4H); 6.00–6.09 (dt, J=10.8 and 6.5 Hz, 1H), 5.66 (dt, J=10.8 and 1.4 Hz, 1H), 3.93 (s, 2H); 3.38 (dd, J=6.9 and 1.3 Hz, 2H); 2.26 (s, 3H) and 1.28 (s, 9H).

(ii) When an ice-cooled solution of N-methyl-N-(1-naphthylmethyl)-2-hydroxy-heptan-4-ynyl-1-amine (II) in DMSO and THF (3:1 v/v) is treated with p-toluenesulfonyl chloride and solid KOH, a 1:4 mixture of E/Z terbinafine is obtained.

(iii) N-Methyl-N-(1-naphthylmethyl)-6.6-(dimethyl-hept-2-en-4-ynyl)-1-amine (II) can be converted to its chloride by reacting with thionyl chloride and pyridine preferably at 0° C. Reaction of the resulting chloride with DBU in DMSO at 100° C. afforded a 1:1 mixture of E/Z terbinafine.

(iv) When a solution of N-methyl-N-(1-naphthylmethyl)-2-hydroxy-heptan-4-ynyl-1-amine (II) in DMSO is heated at 100° C. for 16 h, a 1:9 mixture of E/Z terbinafine is obtained.

(v) When a solution of N-methyl-N-(1-naphthylmethyl)-2-hydroxy-heptan-4-ynyl-1-amine (II) in DMSO containing silica gel and p-toluenesulfonic acid is heated at 100° C. for 16 h, a 1:1 mixture of E/Z terbinafine is obtained.

(vi) When a solution of N-methyl-N-(1-naphthylmethyl)-2-hydroxy-heptan-4-ynyl-1-amine (II) in toluene containing Amberlyst 15 is heated at 100° C. for 36 h, a mixture of E/Z terbinafine is obtained.

EXAMPLE IV
2-[N-methyl-N-naphthylmethyl]-dimethoxyethane (IV)

This reaction can be carried out according to the procedure described in Sandler and Karo. In an ice-cooled flask containing N-methyl-1-naphthalenemethylamine hydrochloride in anhydrous toluene is added 2 equivalents of sodium hydroxide followed by dropwise addition of bromoacetaldehyde dimethoxy acetal. The reaction mixture is then heated in a water bath at 80° C. for 4 h then is cooled to room temperature. The reaction mixture is washed with brine, dried over sodium sulfate, filtered and concentrated in vacuo. Purification of the residue by column chromatography on silica gel with a 10% EtOAc and hexane affords the title compound (IV).

In a similar manner, the reaction of N-methyl-1-naphthalenemethylamine hydrochloride with bromoacetaldehyde ethylene acetal gives methylnaphthylmethyl-[1,3]-dioxolan-2-ylmethylamine.

EXAMPLE V
2-[N-methyl-N-naphthylmethyl]-acetaldehyde (V)

(i) This reaction can be carried out according to the procedure described in Sandler and Karo. In an ice-cooled flask containing N-methyl-1-naphthalenemethylamine hydrochloride in anhydrous toluene is added 2 equivalents of sodium hydroxide followed by dropwise addition of bromoacetaldehyde dimethoxy acetal. The reaction mixture is then heated in a water bath at 80° C. for 4 h then is cooled to room temperature. A 1:1 mixture of concentrated HCl and water is added and the reaction mixture is stirred at room temperature for 16 h. The aqueous layer is separated and the toluene layer is extracted twice with 10% hydrochloric acid. The combined aqueous layers is cooled and made alkaline with 40% sodium hydroxide solution, then extracted with ethyl acetate. The organic layer is collected, dried over sodium sulfate, filtered and concentrated in vacuo. Purification by column chromatography on silica gel using 10% EtOAc and hexane affords the title compound (V).

Similar results are obtained when bromoacetaldehyde ethylene acetal is used as the alkylating reagent.

(ii) The procedure taken from Greene, is used. A mixture of 2-[N-methyl-N-naphthylmethyl]-dimethoxyethane in acetone and catalytic amount of p-toluenesulfonic acid is stirred at room temperature for 24 h. The reaction mixture is made alkaline with triethylamine and volatile materials are removed in vacuo. The residue is purified by column chromatography on silica gel using 10% EtOAc and hexane to give the title compound (V).

EXAMPLE VI
N-Methyl-N-(1-naphthylmethyl)-6.6-(dimethyl-hept-2-en-4-vnyl)-1-amine (i) This reaction is carried out according to the procedure of Corey et. al. n-BuLi is added to a solution of 4,4-dimethylpent-2-ynyl phosphonium bromide in dry THF at −20° C. The mixture is stirred under nitrogen for 30 min, and a solution of 2-[N-methyl-N-naphthylmethyl]-acetaldehyde in THF is added. The resulting mixture is stirred at room temperature for 5 h, then quenched by addition of saturated ammonium chloride solution and extracted with ethyl acetate. The organic layer is dried over sodium sulfate and evaporated to give an oil. Column chromatography (5% EtOAc; hexane) gives the title compound as E/Z mixture.

(ii) In a similar fashion, an E/Z mixture of the title compound can be obtained by reacting a solution of 2-[N-methyl-N-naphthylmethyl]-acetaldehyde in THF with the reagent (VII).

The embodiment of the present invention in which exclusive properties and rights are claimed are defined as follows:

1. A process for the manufacture of compounds of formula I:

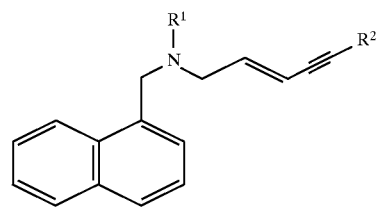
(I)

wherein
$R^1$ is lower alkyl,
$R^2$ is alkyl, arylalkyl,
which comprises the following steps:
(a) reacting N-alkyl-N-naphthylmethylamine with epichlorohydrin to give a compound of formula (III) in presence of base and alcohol; and

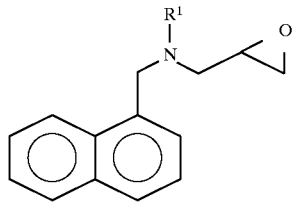
(III)

wherein $R^1$ is as defined above,
(b) reacting the compound of formula (III) with lithium alkylacetylide in the presence of lewis acid to give a compound of formula (II); then

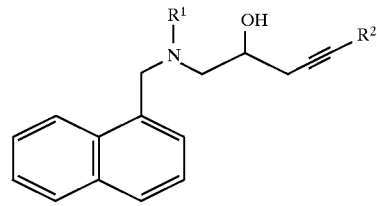
(II)

wherein $R^1$ and $R^2$ are as defined above,
(c) dehydrating compound of formula (II) into a compound of formula (I).

2. A process of claim 1 wherein the base is metal hydroxide or alkoxide or a phase transfer reagent.

3. A process of claim 2 wherein the alcohol is a saturated alcohol having 1 to 6 carbon atoms.

4. A process of claim 3 wherein the lewis acid is boron trifluoride etherate.

5. A process of claim 4 wherein $R^1$ is methyl.

6. A process of claim 5 wherein $R^2$ is 1,1-dimethylethyl.

7. A process for the manufacture of compounds of formula (I):

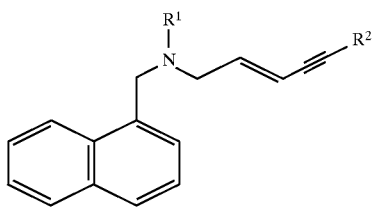
(I)

wherein
$R^1$ is lower alkyl,
$R^2$ is alkyl, arylalkyl,
which comprises the following steps:
(i) reacting N-alkyl-N-naphtylmethylamine with bromoacetaldehyde dialkylacetal in the presence of a base to give a compound of formula (IV); and

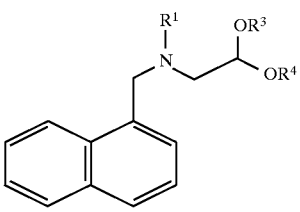
(IV)

wherein
$R^1$ is as defined above,
$R^3$ and $R^4$ are each independently alkyl,
(ii) submitting the compound of formula (IV) to an acid hydrolysis to give compound (V); and

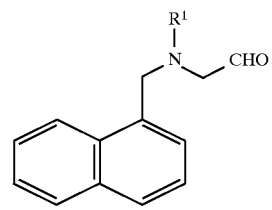
(V)

wherein $R^1$ is as defined above,
(iii) reacting the compound of formula (V) with:
(a) either a Wittig reagent of formula (VI);

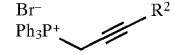
(VI)

wherein $R^2$ is as defined above, or
(b) a compound of formula (VII);

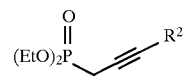
(VII)

wherein $R^2$ is as defined above.

8. The process of claim 7, wherein the base is selected from the group consisting of sodium hydroxide and potassium carbonate.

9. The process of claim 7, wherein the acid is hydrochloric acid.

10. The process of claim 7, wherein the acid hydrolysis of compound IV to compound V is made with acetone in the presence of p-toluenesulfonic acid at room temperature.

11. A process for the manufacture of terbinafine which comprises the following steps:
a. reacting N-methyl-N-naphthylmethylamine with epichlorohydrin to give N-methyl-N-naphthylmethyl-2,3-epoxypropane (III) in the presence of a base and an alcohol;

b. reacting N-methyl-N-naphthylmethyl-2,3-epoxypropane (III) with lithium tert-butylacetylene to give N-Methyl-N-(1-naphthylmethyl)-6,6-dimethyl-2-hydroxyheptan-4-ynyl-1-amine (II);

c. converting N-Methyl-N-(1-naphthylmethyl)-6,6-dimethyl-2-hydroxyheptan-4-ynyl-1-amine (II) to terbinafine.

12. The process of claim 11, wherein the base is selected from the group consisting of metal hydroxide, metal alkoxide and a phase transfer reagent.

13. A process of claim 11, wherein the temperature of the reaction is maintained within the range of 60° C. to 80° C.

14. A process of claim 11, wherein the alcohol is a saturated alcohol having one to 6 carbon atoms.

15. A process of claim 11, wherein the reaction b is done in the presence of boron trifluoride etherate.

16. A process of claim 11, wherein the conversions of N-methyl-N-(1-naphthylmethyl)-6,6-dimethyl-2-hydroxyheptan-4-ynyl-1-amine to terbinafine is made with methanesulfonyl chloride or toluenesulfonyl chloride in the presence of base.

17. A process of claim 16, wherein the base is selected from the group consisting of triethylamine, DBU, tert-butoxide and potassium hydroxide.

18. A process according to claim 11, wherein the conversion of N-methyl-N-(1-naphthylmethyl)-6,6-dimethyl-2-hydroxy-heptan-4-ynyl-1-amine to terbinafine is a dehydration obtained either: (i) by heating N-Methyl-N-(1-naphthylmethyl)-6,6-dimethyl-2-hydroxy-heptan-4-ynyl-1-amine (II) with an acid in an organic solvent; or (ii) by heating N-Methyl-N-(1-naphthylmethyl)-6,6-dimethyl-2-hydroxy-heptan-4-ynyl-1-amine in dimethyl sulfoxide (DMSO).

19. A process of claim 1 which comprises of the following steps:

a. reacting of N-alkyl-N-naphthylmethylamines with bromo acetaldehyde dialkyl acetal to give 2-[N-alkyl-N-naphthylmethyl]-1,1-dialkoxyethane, a compound of formula (IV) in presence of base;

b. reacting of 2-[N-alkyl-N-naphthylmethyl]-1,1-dialkoxyethane, a compound of formula (IV) with acid to give a compound of formula V;

c. reacting of a compound of formula V with a compound of formula VI to give a compound of formula I.

20. The process according to claim 18 wherein the organic solvent is dimethyl sulfoxide or toluene.

21. The process according to claim 18 wherein the heating is at 110° C.

* * * * *